United States Patent
Shalaby

(10) Patent No.: US 9,248,094 B2
(45) Date of Patent: Feb. 2, 2016

(54) SUTURE-SPECIFIC COATINGS FOR MODULATED RELEASE OF BIOACTIVE AGENTS

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 1390 days.

(21) Appl. No.: 11/980,163

(22) Filed: Oct. 30, 2007

(65) Prior Publication Data

US 2008/0102104 A1    May 1, 2008

Related U.S. Application Data

(60) Provisional application No. 60/855,298, filed on Oct. 30, 2006.

(51) Int. Cl.

| | |
|---|---|
| *A61F 2/00* | (2006.01) |
| *A61K 9/00* | (2006.01) |
| *A61K 9/70* | (2006.01) |
| *A61K 31/335* | (2006.01) |
| *A61K 31/42* | (2006.01) |
| *A61K 47/34* | (2006.01) |
| *A61L 17/14* | (2006.01) |
| *A61K 31/74* | (2006.01) |
| *A61L 17/10* | (2006.01) |
| *A61L 17/06* | (2006.01) |
| *A61K 47/30* | (2006.01) |
| *A61K 31/765* | (2006.01) |
| *A61L 17/00* | (2006.01) |
| *A61L 17/12* | (2006.01) |

(52) U.S. Cl.
CPC .............. *A61K 9/0024* (2013.01); *A61K 9/7007* (2013.01); *A61K 31/335* (2013.01); *A61K 31/42* (2013.01); *A61K 47/34* (2013.01); *A61L 17/005* (2013.01); *A61L 17/145* (2013.01); *A61K 31/74* (2013.01); *A61K 31/765* (2013.01); *A61K 47/30* (2013.01); *A61L 17/00* (2013.01); *A61L 17/06* (2013.01); *A61L 17/10* (2013.01); *A61L 17/12* (2013.01); *A61L 2300/202* (2013.01); *A61L 2300/404* (2013.01); *A61L 2300/416* (2013.01); *A61L 2300/602* (2013.01); *A61L 2300/606* (2013.01)

(58) Field of Classification Search
None
See application file for complete search history.

(56) References Cited

U.S. PATENT DOCUMENTS

| | | | |
|---|---|---|---|
| 4,461,298 A | 7/1984 | Shalaby | |
| 5,378,540 A * | 1/1995 | Olson | 428/394 |
| 5,522,842 A | 6/1996 | Shalaby | |
| 5,773,563 A | 6/1998 | Shalaby | |
| 6,462,169 B1 | 10/2002 | Shalaby | |
| 6,498,229 B1 | 12/2002 | Shalaby | |
| 6,703,035 B2 | 3/2004 | Shalaby | |
| 6,794,485 B2 * | 9/2004 | Shalaby et al. | 528/354 |
| 7,026,437 B2 | 4/2006 | Shalaby | |
| 2002/0114840 A1 * | 8/2002 | Shalaby | 424/486 |
| 2003/0219562 A1 * | 11/2003 | Rypacek et al. | 428/36.91 |
| 2005/0251249 A1 * | 11/2005 | Sahatjian et al. | 623/1.46 |
| 2006/0193884 A1 * | 8/2006 | Stopek et al. | 424/422 |

* cited by examiner

*Primary Examiner* — James Rogers
(74) *Attorney, Agent, or Firm* — McNair Law Firm, P.A.; Douglas L. Lineberry

(57) ABSTRACT

Suture-specific coatings having a number average molecular weight not exceeding 20 kDa, a melting temperature above 37° C., and heat of fusion exceeding 20 J/g, are formed of copolyesters of polycaprolactone or of ε-caprolactone and at least one cyclic monomer forming a segmented polyester chain initiated by a polyaxial crystalline organic compound or an amorphous polyaxial polymeric initiator and include from about 0.01 to about 10 weight percent of at least one molecularly dispersed bioactive agent.

16 Claims, No Drawings

SUTURE-SPECIFIC COATINGS FOR MODULATED RELEASE OF BIOACTIVE AGENTS

The present application claims the benefit of prior U.S. provisional application Ser. No. 60/855,298, filed Oct. 30, 2006.

FIELD OF THE INVENTION

This invention relates to a new approach to coating surgical sutures, not only to improve their surface aesthetics and handling characteristics and reduce capillarity of braided multifilaments, but also to allow their use as vehicles for the controlled release of bioactive agents to enhance or augment the suture performance as a tissue repair device. The polymeric coating is designed to meet certain requirements as to the interfacial chemicophysical compatibility with the suture, solubility in an easy-to-apply organic solvent, achieving and maintaining molecular dispersity of at least one active agent in the coating and controlling the release profile of the at least one active agent.

BACKGROUND OF THE INVENTION

Surface coating of sutures and allied medical products has been the subject of extensive interest in the prior art as it relates mostly to improved surface aesthetics and handling characteristics and reduction of capillarity in braided multifilaments as reviewed in U.S. Pat. No. 4,461,298 (1984), which was uniquely directed to minimizing the tissue-reaction encountered in commercially available silk sutures due to components of commonly used silk suture coatings. Several reports of the prior art also addressed the use of coating on multifilament braided sutures as a vehicle for the controlled release of antimicrobial agents, among others which have been randomly described, in part, in a number of patents including U.S. Pat. Nos. 3,987,797; 4,027,676; 4,105,034; 4,185,637; 4,201,216; and 4,461,298. In effect, the selections of the coatings, with or without bioactive agents, as described in the prior art were based primarily on a trial-and-error approach without integrating conceptual designs of useful (1) surface coatings tailored for specific suture geometry (being a monofilament or multifilament) and unique surface chemistry (being polar or non-polar and permanent or transient); (2) coatings that are capable of predictable and controllable release of a specific agent based on molecular dispersity of such an agent in the polymer; (3) coatings that can be easily and reproducibly applied to the suture without compromising its initial physicomechanical properties; (4) coatings that do not chemically react with an added bioactive agent and alter its intended bioactivity; and (5) coatings that can be used as a vehicle for incorporating at least one bioactive agent in a molecularly dispersed form while remaining independently efficacious. Reviewing the noted deficiencies of the prior art and availability of patented polymeric compositions developed in this laboratory, including those on polyesters displaying autocatalyzed hydrolysis and segmented polyaxial and linear copolyesters (U.S. Pat. Nos. 5,522,842; 5,773,563; 6,462,169; 6,498,229; 6,703,035; 6,794,485; 7,026,437; and 7,070,858), and acknowledging the growing interest in meeting the surgical needs of a broad spectrum of patients of acknowledged diversity in age and ailment provided a strong incentive to pursue the subject of the present invention. Indeed, the subject invention uniquely integrates key chemical, physicomechanical, biological, and pharmacological aspects pertinent to the use of drug-containing coatings to produce highly efficacious suture products having suture-specific coatings for modulated release of at least one bioactive agent.

SUMMARY OF THE INVENTION

This invention deals in general with a suture-specific coating, soluble in at least one common organic solvent, which is a crystalline, polyaxial copolyester of polycaprolactone or a copolyester of $\epsilon$-caprolactone and at least one cyclic monomer selected from the group consisting of lactide, glycolide and trimethylene carbonate, the copolyester having a weight average molecular weight not exceeding 20 kDa, exhibiting a melting temperature ($T_m$) above 37° C., and a heat of fusion ($\Delta H_f$) exceeding 20 J/g, and containing 0.01 to 15 weight percent of at least one molecularly dispersed bioactive agent selected from the groups known for their antimicrobial, antiviral, antineoplastic, anti-inflammatory, pain-relieving, anesthetic and tissue regenerative activity, and using a coating level suitable for the controlled release of the agent for a period exceeding three days and two weeks for monofilament and braided multifilament suture, respectively.

A specific aspect of the present invention is a coating that is tailored for use with an absorbable, braided multifilament suture which is formed of a high-glycolide, segmented, polyaxial copolyester, wherein the coating itself is a polyaxial copolyester made by end-grafting an amorphous, monocentric triaxial copolymeric initiator of about 90/10 (molar) trimethylene carbonate/$\epsilon$-caprolactone with about 95/5 $\epsilon$-caprolactone/glycolide and containing (1) more than about 2 weight percent of the antimicrobial agent triclosan and using a coating level suitable for the controlled release of efficacious amounts of said agent over a period exceeding two weeks, or (2) less than 10 weight of an antineoplastic agent selected from the group represented by leflunamide and paclitaxel and using a coating level suited for the controlled release of efficacious amounts of said agent over a period exceeding two weeks.

Another specific aspect of the present invention is a coating that is tailored for use with an absorbable, compliant monofilament suture which is a high-glycolide segmented linear copolyester, wherein the coating itself is a polyaxial copolyester made by end-grafting an amorphous monocentric triaxial copolymeric initiator of about 85/15 (molar) trimethylene carbonate/$\epsilon$-caprolactone end-grafted with about 95/5 $\epsilon$-caprolactone/glycolide, and having more than about 2 weight percent of the antimicrobial agent triclosan, wherein the coating is applied at a level suitable for the controlled release of efficacious amounts of said agent over a period exceeding three days.

Another aspect of this invention relates to a coating that is tailored for use with an absorbable braided multifilament suture which is a high lactide, segmented, linear copolyester wherein the coating itself is a polyaxial copolyester made by the ring-opening polymerization of about 95/5 $\epsilon$-caprolactone/glycolide mixture in the presence of triethanolamine and stannous octanoate as the initiator and catalyst, respectively, and contains more than about 2 weight percent of the antimicrobial agent triclosan and is applied at a level suitable for the controlled release of efficacious amounts of said agent over a period exceeding two weeks.

An important aspect of this invention is a coating that is tailored for use with an absorbable monofilament suture which is a high lactide, segmented, polyaxial copolyester wherein the coating itself is a polyaxial copolyester made by the ring-opening polymerization of about 95/5 $\epsilon$-caprolactone/glycolide mixture in the presence of triethanolamine and stannous octanoate as the initiator and catalyst, respectively, containing more than about 2 weight percent of the antimicrobial agent triclosan and is applied at a level suitable for the controlled release of efficacious amounts of said agent over a period exceeding three days.

Another specific aspect of the present invention is a coating that is tailored for use with a degummed multifilament braided, dyed or undyed, silk suture wherein the coating itself is a polyaxial copolyester made by end-grafting an amorphous monocentric, triaxial copolymeric initiator, prepared by the ring-opening polymerization of about 90 percent by mole of trimethylene carbonate and about 10 percent by mole of $\epsilon$-caprolactone in the presence of trimethylolpropane and stannous octanoate, with a mixture of about 95 percent by mole of $\epsilon$-caprolactone and about 5 percent by mole of l-lactide, the resulting copolyester having molecularly dispersed therein greater than about 2 weight percent of an antimicrobial agent comprising triclosan, wherein the coating is applied to a multifilament braided silk suture at a level suitable for the controlled release of efficacious amounts of said agent over a period exceeding three weeks.

Another key aspect of this invention deals with a coating that is tailored for use with a non-absorbable monofilament suture formed of at least one polymer selected from the group represented by a linear aliphatic polyamide, a polyalkylene terephthalate-polyether segmented copolymer, and polypropylene, wherein the coating itself is a polyaxial copolyester made by the ring-opening polymerization of $\epsilon$-caprolactone in the presence of trimethylolpropane and stannous octanoate as the initiator and catalyst, respectively, containing more than about 2 weight percent of the antimicrobial agent triclosan and is applied at a level suitable for the controlled release of efficacious amounts of said agent over a period exceeding three days.

A major aspect of this invention relates to a coating that is tailored for use with a non-absorbable multifilament braided suture formed of at least one polymer selected from the group represented by a linear aliphatic polyamide, a linear aromatic polyester, polypropylene, and ultrahigh molecular weight polyethylene, wherein the coating itself is a polyaxial copolyester made by the ring-opening polymerization of $\epsilon$-caprolactone in the presence of trimethylolpropane and stannous octanoate as the initiator and catalyst, respectively, containing more than about 2 weight percent of the antimicrobial agent triclosan and is applied at a level suitable for the controlled release of efficacious amounts of said agent over a period exceeding two weeks.

A clinically important aspect of this invention deals with a suture-specific coating applied to a suture, sterilized, and packaged for use in tissue repair requiring reliable ligation over a period ranging from one to eight weeks.

The concept of multifilament braided suture-specific coatings for modulating the release of bioactive agents can be further extended to cover allied surgical constructs, namely, one-component meshes made from the same type of multifilament yarn associated with any specific coating discussed above.

DETAILED DESCRIPTION OF PREFERRED EMBODIMENTS

This invention deals with a new approach to coating sutures that differs from those of the prior art. In effect, practically all approaches of the prior art relied on experimental trial and error to develop suture coating with improved surface aesthetic and handling characteristics while reducing capillarity of braided sutures to prevent harboring bacteria and the likelihood of infection. More specifically, one aspect of the present invention uses tailor-made surface coatings that meet the long sought and partially unfulfilled total requirements of a suture coating. These include (1) surface lubricity and low friction coefficient of sliding suture strands during knot tie-down while maintaining adequate security of suture knot against untying under prevailing biological conditions and forces when used in tissue ligation; (2) reduction of braid capillarity at minimum coating levels through selecting polymeric coatings exhibiting minimum interfacial tension relative to the polymeric material of the uncoated multifilament; (3) application of needed coating loading without compromising the drapiness and engineering compliance characteristics of most braid constructions, through selecting polyaxial coating materials that are known to exhibit a limited degree of crystallinity and form small crystallites; and (4) application of effective coating levels on monofilament sutures without encountering scuffing and delamination during knot tie-down by selecting coating materials that are physicochemically compatible with the monofilament substrate due to minimized interfacial tension between them. Generally, monofilaments represent an ignored class of coated surgical sutures because of their low surface to volume ratio.

Longstanding interest in producing antimicrobial sutures, along with contemporary calls for the so-called active sutures for a growing diversity in patient ailments and consistently uncovered complications with wound healing, have led many investigators of the prior art to randomly incorporate, without scientific or theoretical bases, a variety of well-established antimicrobial agents regardless of their physicochemical properties in available suture coatings, while assembling active coating formulations for their controlled release. Unfortunately, most investigators of the prior art overlooked the basic tenets for developing a drug release system with modulated release profile consistent with the biological site requirements. Among the key factors relevant to those tenets, which also constitutes the basis of the present invention, are (1) chemical biocompatibility of the active agent(s) with the coating polymer to prevent unwanted chemical reactions, which may alter the intended activity and potency of the drug; (2) avoidance of having drug particulates with uncontrollable size, and hence, variable solubility and degree of diffusion through the coating matrix—this led to the use of molecularly dispersed active agent(s) in the coatings, subject of this invention, where drug molecules diffuse outwardly in practically independent fashion to insure reproducible availability at the biological site; and (3) production of active monofilament sutures, unique to the present invention, where the drug molecular dispersity allows the use of adequate loading of active agents without compromising active physicomechanical compatibility described above as a key feature of the present invention.

Among the key aspects stressed in this invention is the use of the chemically tailored coatings for specific active agents to achieve the controlled release of agents other than the antimicrobials frequently disclosed in the prior art. The relatively unexplored bioactive agents include those known for their antineoplastic, antiviral, anti-inflammatory, pain-relieving, and anesthetic, and tissue-growth promoting activities.

A key aspect of this invention is the integration of the unique features of the structurally tailored materials relative to the suture surface with unique features of the drug physicochemical properties selected to provide a totally integrated suture-specific coating for the modulated release of bioactive agents.

Further illustrations of the present invention are provided by the following examples:

Example 1

General Methods of Preparation and Characterization of Crystalline Segmented Polyaxial Copolyesters Using Amorphous Polymeric Initiator and Composition of Representative Polymers General Methods—

The procedures described in U.S. Pat. No. 6,462,169, incorporated herein in its entirety by reference, on segmented crystalline copolymer based on amorphous polymeric initiators were adopted for the preparation of this class of polymers in the form of low molecular weight coating materials for use as carriers of the bioactive agents subject of this invention. Accordingly, a polyaxial prepolymer of 90/10 trimethylene carbonate/ε-caprolactone was first prepared using stannous octanoate as the catalyst and triethanolamine or trimethylolpropane as the monomeric initiator at such a stoichiometry so as to form amorphous polymeric initiator i-PX-AN or i-PX-AC, respectively, for end-grafting with a mixture of ε-caprolactone (CL) and glycolide (G) to produce crystalline polyaxial segmented copolyesters PX-ANG and PX-ACG, respectively, or a mixture of ε-caprolactone and 1-lactide (l-L) to produce PX-ANL and PX-ACL, respectively, having a weight average molecular weight of 10 to 20 kDa. The resulting polymers, PX-ANG, PX-ACG, PX-ANL, and PX-ACL, were purified by precipitating a concentration acetone solution in cold 2-propanol. After isolation of the polymer by filtration and drying at 25-80° C. to a constant weight under reduced pressure, the purified polymers were then characterized for molecular weight by GPC with dichloromethane (DCM) as the mobile phase, differential scanning calorimetry (DSC) for thermal properties, and infrared for identity.

Representative Polymers—

Two representative polymers of type PX-ANG, namely PX-ANG1 and PX-ANG2, were prepared using triethanolamine as the monomeric initiator, stannous octanoate as the catalyst, and a mixture of about 90/10 and about 85/15 trimethylene carbonate/ε-caprolactone (TMC/CL), to prepare the amorphous polymeric initiator i-PX-AN1 and i-PX-AN2, respectively, which were then end-grafted separately with a mixture of about 95/5 ε-caprolactone/glycolide (CL/G). Similarly, a representative example of polymer type PX-ACL, namely PX-ACL1, was prepared by first preparing the polymeric initiator i-PX-AC using about a 90/10 mixture of TMC/l-lactide, which was then end-grafted with about a 95/5 mixture of CL/l-L. The three representative copolyesters, PX-ANG1, PX-ANG2, and PX-ACL1, were found to exhibit the following general properties:

$T_m > 37°$ C., $\Delta H_f > 20$ J/g, and $M_w \leq 20$ kDa

Example 2

General Methods of Preparation and Characterization of Crystalline Segmented Polyaxial Polyester and Composition of Representative Polymers General Methods—

The general procedures described in U.S. patent application Ser. No. 10/128,121, incorporated in its entirety herein by reference, dealing with ε-caprolactone copolyesters were adapted for the tailored preparation of this class of polymeric, low molecular weight coating materials for use as carriers of bioactive agents subject of this invention. Accordingly, monomeric polyaxial initiators, namely, triethanolamine or trimethylolpropane were used to prepare segmented polyaxial copolyester types PX-NG and PX-CG, respectively, using stannous octanoate as the catalyst for the ring-opening polymerization of a mixture of ε-caprolactone and glycolide or lactide at such a monomer/initiator ratio to produce copolymers having a weight average molecular weight ($M_w$) of 10 to 20 kDa. The resulting polymer types, PX-NG and PX-CG, were purified and characterized as generally described in Example 1.

Representative Polymers—

Two representative polymers of types PX-NG and PX-CG were prepared using triethanolamine and trimethylolpropane as the initiators, respectively, and stannous octanoate as the catalyst. One representative polymer of type PX-NG, namely PX-NG1, was prepared using triethanolamine as the initiator and a mixture of about 95/5 ε-caprolactone/glycolide as the cyclic monomers. On the other hand, one representative polymer of type PX-CG, namely PX-CG1, was prepared using trimethylolpropane as the initiator and a mixture of about 95/5 ε-caprolactone/lactide as the cyclic monomers. The monomer/initiator ratio used in the preparation of PX-NG1 and PX-CG1 were adjusted to produce coating materials exhibiting the following properties:

$T_m > 37°$ C., $\Delta H_f > 20$ J/g, and $M_w \leq 20$ kDa

Example 3

Synthesis and Characterization of Polyaxial Poly-ε-caprolactone

General Methods—

Polyaxial poly-ε-caprolactone (PCL-X) was prepared by ring-opening polymerization of ε-caprolactone in the presence of trimethylolpropane and stannous octanoate as the initiator and catalyst, respectively, using a similar process to those disclosed in U.S. Pat. No. 5,522,842, incorporated by reference herein in its entirety. However, the monomer/initiator ratio was adjusted to produce a purified polymeric coating material having a weight average molecular weight of 10 to 20 kDa for use as a carrier of the bioactive agents used particularly in conjunction with synthetic, non-absorbable monofilament and multifilament braided sutures. The purification and characterization of the polymers were conducted as generally described in Example 1. A representative PCL-X exhibited the following properties:

$T_m > 37°$ C., $\Delta H_f > 20$ J/g, and $M_w \leq 20$ kDa

Example 4

General Coating Method and Representative Suture/Bioactive Coating Combination and Testing of Coated Sutures Coating Methods—

A concentrated solution (1 to 50 weight/volume percent) of the bioactive agent was made using the same solvent known to dissolve the polymeric coating or a solvent that is physicochemically compatible with the polymer solution, provided that any used solvent could be easily removed from the coated suture without compromising its physicomechanical properties to any significant extent. The solution of the bioactive agent was mixed thoroughly with a previously made solution of the polymer (5 to 20 weight/volume percent). The suture was coated by threading through the drug/polymer combined solution at room temperature, at a controlled rate to achieve a predetermined add-on. The coated suture was dried in-line by passing through a circulating heated-air oven.

Residual solvent was removed by heating the spooled suture under reduced pressure until a constant weight was attained.

Testing of Coated Sutures—

The coated sutures were tested for (1) coating percent add-on; (2) knot tie-down characteristics; (3) in vitro drug release of bioactive agent used HPLC methods; and (4) in vitro bioactivity using the appropriate cell culture.

Example 5

In Vitro Evaluation of Representative Suture/Bioactive Coating Combination

A representative set of coated sutures was prepared to exhibit antimicrobial or antineoplastic activities. In a typical set of experiments, representative sutures coated with specific polymers containing triclosan were evaluated for their antimicrobial activity toward *S. aureus* using the Zone-of-Inhibition method. Results of these experiments are summarized in Table I. The set entails (1) polypropylene monofilament suture (PP-M); (2) high-lactide, segmented, polyaxial, monofilament suture (LX-M); (3) absorbable, high-glycolide, segmented polyaxial, multifilament braided suture (GX-Br); and (4) silk suture (S—Br).

TABLE I

Composition and In Vitro Evaluation of Coated Suture Antimicrobial Activity[a]

| Suture | Coating | | % of Triclosan in | Duration of |
|---|---|---|---|---|
| Type | Type | % Add-on | Coating | Activity |
| PP-M | PCLX | 0.5 | 10 | 7 days |
| LX-M | PX-NG1 | 1.2 | 10 | 7 days |
| GX-Br | PX-NG1 | 5.5 | 10 | 21 days |
| S-Br | PX-ACL1 | 9.7 | 3 | 21 days |

[a]Using the Zone-of-Inhibition method

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A polymeric coating for a suture, comprising:
   a segmented crystalline block, polyaxial copolyester, wherein the segmented crystalline block, polyaxial copolyester consists of an amorphous prepolymer core and a crystalline end graft, produced by the ring-opening polymerization of a mixture of about 90 mole percent trimethylene carbonate and about 10 mole percent ε-caprolactone in the presence of a triaxial initiator and a catalyst to form a prepolymer, followed by end grafting the prepolymer with a mixture of about 95 mole percent ε-caprolactone and about 5 mole percent glycolide, the copolyester having a weight average molecular weight of up to about 20 kDa, a melting temperature (Tm) of greater than about 37° C., and a heat of fusion (ΔHf) of greater than about 20 J/g, and
   at least one bioactive agent molecularly dispersed in the copolyester, the at least one bioactive agent present in an amount of from about 0.01 to about 15 weight percent, wherein the bioactive agent is selected from the group consisting of antimicrobial agents, antiviral agents, antineoplastic agents, anti-inflammatory agents, pain-relieving agents, anesthetic agents and tissue-regenerative agents.

2. The polymeric coating for a suture as set forth in claim 1 wherein the copolyester has molecularly dispersed therein greater than about 2 weight percent of an antimicrobial agent.

3. The polymeric coating for a suture as set forth in claim 1 wherein the copolyester has molecularly dispersed therein up to about 10 weight percent of an anti-neoplastic agent.

4. The polymeric coating for a suture as set forth in claim 1 wherein the coating is applied to an absorbable, braided multifilament suture comprising a lactide containing, segmented, polyaxial copolyester.

5. The polymeric drug carrier, suture-specific coating as set forth in claim 2 wherein the antimicrobial agent is triclosan.

6. The polymeric coating for a suture as set forth in claim 5 wherein the catalyst is stannous octanoate.

7. The polymeric coating for a suture coating as set forth in claim 6 wherein the triaxial initiator is triethanolamine, and wherein the coating is applied to an absorbable, braided multifilament suture comprising a lactide containing, segmented, linear copolyester.

8. The polymeric coating for a suture as set forth in claim 6 wherein the triaxial initiator is triethanolamine, and wherein the coating is applied to an absorbable monofilament suture comprising a lactide containing, segmented, polyaxial copolyester.

9. The polymeric coating for a suture as set forth in claim 5 wherein the triaxial copolymeric initiator is trimethylolpropane.

10. The polymeric coating for a suture as set forth in claim 9 wherein the coating is applied to a non-absorbable monofilament suture comprising at least one polymer selected from the group consisting of a linear aliphatic polyamide, a polyalkylene terephthalate-polyether segmented copolymer, and polypropylene.

11. The polymeric coating for a suture as set forth in claim 9 wherein the coating is applied to a non-absorbable multifilament braided suture comprising at least one polymer selected from the group consisting of a linear aliphatic polyamide, a linear aromatic polyester, and polypropylene.

12. The polymeric coating for a suture as set forth in claim 1 applied to a suture, sterilized, and packaged for use in tissue repair.

13. A polymeric coating for a suture consisting of:
   a segmented crystalline block, polyaxial copolyester, wherein the segmented crystalline block, polyaxial copolyester consists of an amorphous prepolymer core and a crystalline end graft and made by the ring-opening polymerization of a mixture of about 90 mole percent trimethylene carbonate and about 10 mole percent ε-caprolactone in the presence of a triaxial initiator and a catalyst to form a prepolymer, followed by end grafting the prepolymer with a mixture of about 95 mole percent ε-caprolactone and about 5 mole percent glycolide, the copolyester having a weight average molecular weight of up to about 20 kDa, a melting temperature ($T_M$) of greater than about 37° C., and a heat of fusion ($\Delta H_f$) of greater than about 20 J/g, and
   at least one bioactive agent molecularly dispersed in the copolyester, the at least one bioactive agent being in an amount of from about 0.01 to about 15 weight percent wherein the bioactive agent is selected from the group consisting of antimicrobial agents, antiviral agents, antineoplastic agents, anti-inflammatory agents, pain-relieving agents, anesthetic agents and tissue-regenerative agents.

14. A coated suture comprising:
an absorbable monofilament suture comprising a lactide, segmented, polyaxial copolyester;
a segmented crystalline block, polyaxial copolyester coating on said suture, wherein the segmented crystalline block, polyaxial copolyester consists of an amorphous prepolymer core and a crystalline end graft made by the ring-opening polymerization of a mixture of about 90 mole percent trimethylene carbonate and about 10 mole percent e-caprolactone in the presence of a polyfunctional initiator and a catalyst to form a prepolymer, followed by end grafting the prepolymer with a mixture of about 95 mole percent ε-caprolactone and about 5 mole percent glycolide, the copolyester having a weight average molecular weight of up to about 20 kDa, a melting temperature ($T_M$) of greater than about 37° C., and a heat of fusion ($\Delta H_f$) of greater than about 20 J/g, and
at least one bioactive agent molecularly dispersed in the copolyester, the at least one bioactive agent being present in an amount of from about 0.01 to about 15 weight percent wherein the bioactive agent is selected from the group consisting of antimicrobial agents, antiviral agents, antineoplastic agents, anti-inflammatory agents, pain-relieving agents, anesthetic agents and tissue-regenerative agents.

15. The polymeric drug carrier, suture-specific coating as set forth in claim 3 wherein the anti-neoplastic agent is selected from leflunamide and paclitaxel.

16. The polymeric drug carrier, suture-specific coating as set forth in claim 9 wherein the copolyester is made in the presence of an initiator and a catalyst comprising stannous octanoate.

\* \* \* \* \*